United States Patent [19]

Jarman et al.

[11] 4,235,966

[45] Nov. 25, 1980

[54] PROCESS FOR THE PRODUCTION OF POLYSACCHARIDE

[75] Inventors: Trevor R. Jarman, Reading, England; John R. W. Govan, Musselburgh, Scotland

[73] Assignee: Talres Development (N.A.) N.V., Netherlands Antilles

[21] Appl. No.: 46,153

[22] Filed: Jun. 6, 1979

[30] Foreign Application Priority Data

Jun. 6, 1978 [GB] United Kingdom ............... 26413/78
Feb. 7, 1979 [GB] United Kingdom ............... 04215/79

[51] Int. Cl.$^3$ ............................................. C12P 19/04
[52] U.S. Cl. .................................. 435/101; 435/172; 435/877; 435/874
[58] Field of Search ........................................ 435/101

[56] References Cited

U.S. PATENT DOCUMENTS

| | | | |
|---|---|---|---|
| 3,346,463 | 10/1967 | Goren | 435/101 |
| 3,856,625 | 12/1974 | Imrie | 435/101 |

*Primary Examiner*—Alvin E. Tanenholtz
*Attorney, Agent, or Firm*—Ostrolenk, Faber, Gerb & Soffen

[57] ABSTRACT

A process for the production of polysaccharide consisting of a partially acetylated variable block copolymer of D-mannuronic and L-guluronic acid residues, comprises cultivating in a nutrient medium therefor a strain of Pseudomonas, which is non-pathogenic to humans, and which has been obtained by treating a non-mucoid species of Pseudomonas, which is non-pathogenic to humans, with a β-lactam or aminoglycoside antibiotic whereby a mucoid strain tolerant to said antibiotic was selected, and isolating from the medium the polysaccharide produced.

7 Claims, No Drawings

PROCESS FOR THE PRODUCTION OF POLYSACCHARIDE

This invention relates to a process for the production of polysaccharide of the alginate type from a microbial source other than *Azotobacter vinelandii*.

Alginic acid, a hydrophilic colloidal carbohydrate acid, is a variable block copolymer composed of D-mannuronic and L-guluronic acid units. Alkali salts of alginic acid are soluble in water and one of the outstanding characteristics of such alginate solutions is their high viscosity at low concentrations. Addition of divalent ions such as calcium or magnesium to the solutions causes gelation. The unique physical properties of alginates give them a wide range of industrial applications as emulsifiers, stabilisers and thickeners. They are of particular use in the food industry, in pharmaceuticals, in paper and textile processing and in agriculture.

Alginates and alginic acid have been commercially obtained by extraction from certain species of seaweed. An alternative source is the microbiological alginate producer *Azotobacter vinelandii*. One other microorganism which has been noted to produced polysaccharide of the alginate type is *Pseudomonas aeruginosa*. The polysaccharide produced by *A. vinelandii* and *P. aeruginosa* is similar to that obtained from seaweeds except that the molecule is partially acetylated.

However, certain problems arise in the production of alginates from *Azotobacter vinelandii*. Strict controls on the fermentation are necessary in order to produce a viscous polymer in high yield at a suitable concentration. *Pseudomonas aeruginosa* is undesirable as a source since it is a human pathogen. Other species of *Pseudomonas*, such as *P. putida* and *P. mendocina* which might be safe sources do not usually produce significant amounts of exopolysaccharide and so cannot normally be used.

We have now found that strains which are tolerant to penicillin antibiotics can, indeed, be used as valuable sources of polysaccharide.

According to the present invention, we provide a process for the production of polysaccharide consisting of a partially acetylated variable block copolymer of D-mannuronic and L-guluronic acid residues, which comprises cultivating in a nutrient medium therefor a strain of *Pseudomonas* which is non-pathogenic to humans and which has been obtained by treating a non-mucoid species of *Pseudomonas*, which is non-pathogenic to humans, with a α-lactam or aminoglycoside antibiotic whereby a mucoid strain tolerant to said antibiotic was selected, and isolating from the medium the polysaccharide produced. Particularly useful species include *P. mendocina*, *P. tabaci* (*P. syringae*) and *P. putida*.

The antibiotic may for example be any penicillin, especially a semisynthetic penicillin derivative, such as a carboxyalkyl or carboxyaralkyl derivative of penicillin. A particularly preferred derivative is carbenicillin (disodium α-carboxybenzyl penicillin), but others include esters, e.g. the indanyloxy ester. Other penicillins include 3-halophenyl penicillins such as cloxacillin and flucloxacillin and their analogues. Aminoglucoside antibiotics include streptomycin, neomycin, gentomycin and tobramycin.

When a non-mucoid species of *Pseudomonas* is plated at high density onto a nutrient medium containing the antibiotic at a concentration which is generally toxic to the microorganism (e.g. in the case of carbenicillin, a concentration of about 600μg/ml depending on the species) and the culture is incubated and then replica plated with further incubation, it is found that a small proportion of the bacteria in the culture (ca. 1%) are not inhibited in their growth, but are found to be tolerant to the antibiotic. Selection of these tolerant variants and further plating onto nutrient media provides mucoid colonies which are able to produce a partially acetylated alginate-type polysaccharide in good yield.

The strain can be cultivated under aerobic conditions in any convenient pseudomonad-supporting medium in which it will grow and produce exocellular polysaccharide. Typical media include complex broths, e.g. a 1% nutrient broth, or a chemically defined medium with a supplementary carbon source of, for example, an alcohol, e.g. glycerol; a sugar, e.g. glucose; or a sugar acid, e.g. gluconic acid. The culture may be effected in batch or continuous mode according to conventional practice. A cultivation temperature of about 30° C. and a pH maintained at about 7.0 during continuous cultivation are suitable.

After fermentation, bacterial cells may be removed from the culture broth by centrifugation and the polysaccharide precipitated by addition of the centrifuged supernatant to a precipitant such as propan-2-ol (3 volumes). The precipitated polysaccharide may then be freezed-dried to give a white fibrous product. When glucose is used as a carbon source in nitrogen-limited continuous culture, 35% or more of the glucose utilised may be converted into polysaccharide.

The following examples illustrate the invention further.

EXAMPLE 1

The minimum inhibitory concentration of carbenicillin for growth of *Pseudomonas putida* NCIB 9494 was determined by streaking a loopful of a culture of the organism grown overnight on nutrient broth (Nutrient Broth No. 2, Oxoid Limited, Basingstoke, Hampshire, RG24 OPW U.K.) plus 0.5% (w/v) yeast extract (supplied by Oxoid Limited) on to nutrient agar plates containing carbenicillin at a range of concentrations from 25 μg/ml to 8,000 μg/ml. The plates were incubated at 30° C. and after overnight incubation, no inhibition of growth had occurred on plates with up to and including 450 μg/ml of carbenicillin, only a few tolerant colonies grew on plates containing 500 or 600 μg/ml carbenicillin and no growth was obtained on plates with 600 μl/ml carbenicillin. On the basis of this result, a series of nutrient agar plastes containing either 500 or 600 μg/ml carbenicillin were inoculated by spreading on 0.1 ml of a culture grown overnight in nutrient broth. These plates were incubated at 30° C. for 24 h and then replica-plated onto Pseudomonas isolation agar (Difco Laboratories, P.O. Box 14, West Molesey, Surrey, KT8 OSE, UK). After a further 24 h incubation at 30° C., both nutrient agar plus carbenicillin and Pseudomonas isolation agar plates were examined for mucoid colonies.

A number of mucoid colonies were observed on Pseudomonas isolation agar plates which were replicated of nutrient agar plates containing 600 μg/ml carbenicillin. They were distinguishable from the parent culture type by this mucoid appearance. One of these mucoid variants was selected and maintained on agar slants of a glucose-mineral salts medium which, after inoculation, were incubated for 24 h at 30° C. and subsequently stored at 4° C.

The selected variant was grown continuously in a 0.6 l continuous culture of the chemostat type (Herbert, Elesworth and Telling, (1956), Journal of General Microbiology 14, 601). The culture medium contained:

| glucose | 20 g/l |
|---|---|
| $(NH_4)_2SO_4$ | 0.6 g/l |
| $MgSO_4 \cdot 7H_2O$ | 0.2 g/l |
| $KH_2PO_4$ | 1.5 g/l |
| NaCl | 0.2 g/l |
| $ZnSO_4 \cdot 7H_2O$ | $0.2 \times 10^{-3}$ g/l |
| $CuSO_4 \cdot 5H_2O$ | $0.2 \times 10^{-3}$ g/l |
| $MnSO_4 \cdot H_2O$ | $0.2 \times 10^{-3}$ g/l |
| $CoCl_2 \cdot 6H_2O$ | $0.2 \times 10^{-3}$ g/l |
| $FeSO_4 \cdot 7H_2O$ | $0.6 \times 10^{-3}$ g/l |
| $CaCl_2 \cdot 2H_2O$ | 0.05 g/l |

The medium was adjusted to pH 5.0 and sterilised by autoclaving at 1 kg cm$^{-2}$ for 1 h. The culture medium was added to the culture at 36 ml.h$^{-1}$ giving a residence time of 17 h. The cultivation temperature was controlled at 30° C. The pH was controlled at 7.0 by the automatic addition of 1 M NaOH. The culture was aerated with an air flow of 600 ml.min$^{-1}$ and a stirring speed of 700 rev.min$^{-1}$.

A steady state was established and a sample of culture broth was withdrawn for analysis after 11 residence times. A portion of this sample was rendered 0.1 M in NaCl and 0.01 M in tetrasodium ethylenediamine tetraacetate (EDTA) and centrifuged for 1 h at 40,000 G. The biomass was estimated by resuspending the sediment in distilled water, recentrifuging and drying the resultant sediment to constant weight at 105° C. The exopolysaccharide was obtained from the supernatant of the first centrifugation by precipitation with isopropanol (3 volumes) and determined by drying the precipitate to constant weight at 45° C. in vacuo. For other purposes, the exopolysaccharide was freeze-dried. Glucose was estimated by the glucose oxidase method.

Determinations on the steady state sample gave biomass, 3.3 gl$^{-1}$, exopolysaccharide 6.3 gl$^{-1}$, residual glucose, 2 gl$^{-1}$. The conversion efficiency for glucose into exopolysaccharide was 35%.

The exopolysaccharide obtained was precipitated from solution on addition of calcium chloride. On acid hydrolysis and subsequent high voltage electrophoresis (as described by A. Haug and B. Larsen, Acta Chemica Scandinavia, 15, 1395-1396. 1961), the exopolysaccharide gave an identical electrophoretogram to sodium alginate and was shown to contain both mannuronic acid and guluronic acid. Determination of the polymeric block composition of the exopolysaccharide (see A. Penman and G. R. Sanderson, Carbohydrate Research, 25, 273-282, 1972) which had been subjected to a deacetylation procedure (A. Linker and L. R. Evans, Carbohydrate Research, 47, 179-187, 1976) indicated that the polysaccharide contained both polyguluronic acid (8%, W/W) and polymannuronic acid (38%, W/W) blocks. An infra-red spectrum of the exopolysaccharide was typical of that obtained from an acetylated alginate-type polysaccharide.

EXAMPLE 2

Mucoid varients of *Pseudomonas mendocina* NCIB 10541 were obtained using the procedure described in Example 1. One such variant was grown in continuous culture of the chemostat type of 2.3 l working volume.

The medium which contained

| glucose | 40 g/l |
|---|---|
| $K_2HPO_4$ | 1.5 g/l |
| $NH_4Cl$ | 1.2 g/l |
| $Na_2SO_4$ | 0.4 g/l |
| $MgCl_2 \cdot 6H_2O$ | 0.2 g/l |
| Citric acid | 0.1 g/l |
| $FeCl_2 \cdot 4H_2O$ | 0.04 g/l |
| $CaCl_2 \cdot 2H_2O$ | 0.004 g/l | was sterilised by autoclaving for 15 minutes at 1 kg cm$^{-2}$. Culture medium was added to the chemostat at 122 ml hr$^{-1}$ giving a residence time of 19 hrs. Cultivation temperature was controlled at 37° C. The pH was controlled at 7.0 by automatic addition of 2 M NaOH. The culture was aerated with an air flow of 2 l min$^{-1}$ and a stirring speed of 500 rev. min$^{-1}$.

After 4½ residence times under the above conditions, a sample was taken which contained exopolysaccharide 4.1 gl$^{-1}$, biomass 3.2 gl$^{-1}$ and residual glucose 17.4 gl$^{-1}$. Conversion efficiency for glucose into exopolysaccharide was 17%. The viscosity of this culture sample was measured on a Wells-Brookfield L.V.T. micro-viscometer at 25° C. The consistency index, K, was 220 cp and the flow index, n, 0.07.

A portion of the above sample was made 0.1 M in NaCl and 0.01 M in EDTA and centrifuged for one hour at 40,000G. The exopolysaccharide in the supernatant was precipitated with 3 volumns isopropanol, filtered off and freeze-dried. A 1% solution of the freeze-dried exopolysaccharide in deionised water was measured for viscosity in the above manner. Consistency index, K was 10,500 cp and the flow index, n, was 0.367. An infra-red spectrum of the exopolysaccharide was typical of an acetylated alginate-type polysaccharide.

We claim:

1. A process for the production of polysaccharide consisting of a partially acetylated variable block copolymer of D-mannuronic and L-guluronic acid residues, which comprises cultivating in a nutrient medium therefor a strain of *Pseudomonas*, which is non-pathogenic to humans, and which has been obtained by treating a non-mucoid species of *Pseudomonas*, which is non-pathogenic to humans, with a β-lactam or aminoglycoside antibiotic whereby a mucoid strain tolerant to said antibiotic was selected, and isolating from the medium the polysaccharide produced.

2. A process according to claim 1, in which the penicillin antibiotic is a carboxyalkyl or carboxyaralkyl derivative of penicillin, an ester thereof or a 3-halophenyl derivative of penicillin.

3. A process according to claim 2, in which the penicillin antibiotic is carbenicillin.

4. A process according to claim 1 in which the strain of *Pseudomonas* has been derived from *P. mendocina, P. tabaci* or *P. putida*.

5. A process according to claim 1, in which the strain used has been obtained by subjecting the mucoid species of *Pseudomonas* to culture on a selective medium containing a generally inhibitory concentration of the antibiotic.

6. A process according to claim 5 in which carbenicillin had been included in the selective medium at a concentration of about 600 μg/ml.

7. A process according to claim 5 using *P. mendocina* or *P. putida*, selected by indicating carbenicillin the selective medium at a concentration of from 500 to 600 μg/ml.

* * * * *